United States Patent [19]

Kahan et al.

[11] 4,135,978
[45] Jan. 23, 1979

[54] PRODUCTION OF N-ACYL-THIENAMYCINS

[75] Inventors: Jean S. Kahan; Frederick M. Kahan, both of Rahway, N.J.

[73] Assignee: Merck & Co., Inc., Rahway, N.J.

[21] Appl. No.: 825,884

[22] Filed: Aug. 19, 1977

[51] Int. Cl.$^2$ .............................................. C12D 13/06
[52] U.S. Cl. ................................................... 195/29
[58] Field of Search ................................... 195/29, 30

[56] References Cited

U.S. PATENT DOCUMENTS

| 3,304,236 | 2/1967 | Nuesch et al. | 195/29 |
| 3,912,589 | 10/1975 | Smith et al. | 195/29 |
| 3,945,888 | 3/1976 | Takahashi et al. | 195/29 |
| 3,950,357 | 4/1976 | Kahan et al. | 195/80 R |
| 3,975,235 | 8/1976 | Niwa et al. | 195/29 |

FOREIGN PATENT DOCUMENTS 939708 10/1963 United Kingdom ................ 195/29

OTHER PUBLICATIONS

Advances in Applied Microbiology, vol. 17, pp. 311-319, (1974).
Journal of Biochemistry, vol. 115, pp. 733-739, (1969).

Primary Examiner—Raymond N. Jones
Assistant Examiner—Robert J. Warden
Attorney, Agent, or Firm—James A. Arno; Julian S. Levitt

[57] ABSTRACT

The disclosed invention is directed to a process for preparing N-acyl-thienamycins from thienamycin and the appropriate acyl group by reacting the same in the presence of certain penicillin amidohydrolases capable of producing N-acyl thienamycins.

8 Claims, No Drawings

PRODUCTION OF N-ACYL-THIENAMYCINS

DESCRIPTION OF THE INVENTION

This invention relates to a process for producing N-acyl-thienamycins.

More particularly, the present invention provides a process for the preparation of N-acyl-thienamycins which process comprises bringing thienamycin and acyl compounds into contact with certain penicillin amidohydrolases wherein N-acyl-thienamycin derivatives are produced.

By penicillin amidohydrolases capable of producing the N-acyl-thienamycins is meant the whole cells of the microorganism that produces an enzyme or mixture of enzymes extracted from these organisms, that causes the acyl compound to react with thienamycin to give the N-acylated thienamycins.

According to the present invention, N-acyl thienamycins having the following structure:

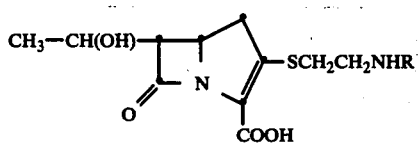

I wherein R is an acyl group, are produced by reacting the compound thienamycin, having the following structure:

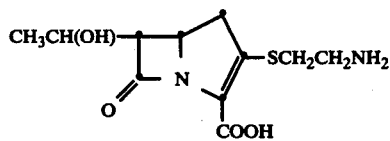

II with an acyl compound, either the carboxylic acid, an amide thereof, a peptide thereof or a lower alkyl ester thereof, in the presence of penicillin amidohydrolases of the category designated E.C. 3.5.1.11 by the International Commission of Enzyme Nomenclature.

DETAILED DESCRIPTION OF THE INVENTION

The method of preparing the N-acyl-thienamycins is by reacting the appropriate acyl compound, either as the carboxylic acid, an amide therof, a peptide therof or a lower alkyl ester thereof with thienamycin either in fermentation broth or an intermediate state of purity. Since the resulting derivatives can be more susceptible to isolation techniques employing organic solvents, they permit recovery of the thienamycin nucleus with higher efficiency from fermentation broths and concentrates. Once the derivatized thienamycin is recovered from the broth or solution, the acyl group can be removed in order to regenerate the thienamycin.

In the generic representation of the compounds of the present invention, (I above), the acyl radical R, can be derived from a saturated or unsaturated, substituted or unsubstituted aliphatic with greater than 5 carbon atoms, aromatic or arylaliphatic carboxylic acid or carbothioic acid. One group of acyl radicals can be represented by the general formula:

wherein X is O or S and R' represents a straight or branched chain alkyl group containing from 5–10 carbon atoms, aryl, aryloxy, typically containing 6–10 carbon atoms. Such above-listed groups can be unsubstituted or can be substituted by radicals such as OH, SH, SR" (R" is loweralkyl or aryl such as phenyl), alkyl or alkoxy groups having 1-6 carbon atoms, halo, such as Cl, Br, F and I, cyano, carboxy, nitro sulfamino, carbamoyl, sulfonyl, azido, amino, substituted amino such as alkylamino including quaternary ammonium wherein the alkyl group comprises 1-6 carbon atoms, haloalkyl such as trifluoromethyl, carboxyalkyl, carbamoylalkyl, N-substituted carbamoylalkyl, wherein the alkyl moiety of the foregoing four radicals comprises 1-6 carbon atoms, amidino, guanidino, N-substituted guanidino, guanidino lower alkyl and the like. Representative examples of such acyl groups that might be mentioned are those wherein R' is benzyl, aminobenzyl, phenoxymethylene, p-hydroxybenzyl, N-amyl, N-heptyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, D-4-N-benzoylamino-4-carboxy-n-butyl, p-aminobenzyl, o-aminobenzyl, m-aminobenzyl, p-dimethylaminobenzyl, 2-ethoxy-1-napthyl, 4-guanidinomethylphenyl, 4-guanidinomethylbenzyl, 4-guanidinobenzyl, 4-guanidinophenyl, 2,6-dimethyoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 2-phenylvinyl, 2-phenylethynyl, phenyl, o-methoxyphenyl, o-chlorophenyl, o-phenylphenyl, or p-aminomethylbenzyl.

The preferred compounds that can be utilized in this invention that fit the above acyl compound description are phenyl acetic acid, p-hydroxyphenyl acetic acid, p-aminophenyl acetic acid, 3-hexenoic acid and the N-glycyl and methyl esters of the above preferred carboxylic acids.

Some examples of these preferred compounds are methylphenyl acetate, methyl p-hydroxyphenyl acetate, methyl p-aminophenyl acetate, methyl 3-hexenoate, N-glycylphenyl acetate, N-glycyl p-hydroxyphenyl acetate, N-glycyl p-aminophenyl acetate and N-glycyl 3-hexenoate. Also included within this preferred group are the amide, N-glycyl or methyl ester of phenylglycine. Some examples of these preferred compounds are N-glycyl phenylglycinate and methyl phenylglycinate.

It is known in the art that penicillin amidohydrolases used on an industrial scale to catalyze the hydrolytic removal of the side chain of penicillin to give the nucleus 6-aminopenicillanic acid (6-APA) can also be used to catalyze the reverse reaction. In the reverse (or synthetic) reaction, 6-APA plus acyl compound in the presence of penicillin amidohydrolase yield penicillin analogs. The synthetic reaction is generally promoted by the use of acyl compounds in the form of their lower alkyl (1–4 carbon atoms) esters present at high concentration and in excess of the 6-APA nucleus. That penicillin amidohydrolase is also capable of generating N-acylated thienamycins from thienamycin and appropriate acyl compounds is surprising. The process of this invention may be conducted by reacting the starting material of the general formula II along with the appropriate acyl compound as the carboxylic acid, an amide thereof, a peptide thereof or a lower alkyl ester thereof, in the presence of the enzyme from an extract of a cultured broth, the filtrate or fermentation product of the Escherichia coli culture or a powder of the enzyme in an aqueous solution. Alternatively, the enzyme may be immobilized by adsorption or chemical reaction to an insoluble supporting structure such as glass, cellulose or agarose, and used to generate N-acylated thienamycins either by contacting it (in the presence of appropriate acyl compounds as the carboxylic acid, an amide thereof, a peptide thereof or a lower alkyl ester thereof) in suspension or by percolation through a bed of immobilized enzyme preparation.

The enzyme is capable of producing N-acyl thienamycins from thienamycin present or produced in fermentation broths as well as from isolated thienamycin.

More particularly, the acylation of theinamycin takes place in the presence of an enzyme of the microorganism of the genus *Escherichia coli* which is capable of producing the N-acylated thienamycins.

For the production of the amidohydrolase enzyme by cultivation of the above-mentioned microorganism, there may be used various culture media commonly employed for the cultivation of a microorganism. More specifically, glucose, sucrose, glycerol, starch, oils used for cultivation and the like as a carbon source and peptone, buillion, corn steep liquor, yeast extract, meat extract, fish meal, defatted soybean, wheat embryo and the like as a nitrogen source may be employed. If required, other additives may be employed in combination with the above. It is an advantage but no a necessity to include phenylacetic acid or its salts or derivatives in fermentation media.

As a cultivation method, *Escherichia coli* is usually shaken or agitated under aeration. Cultivation temperature may range from about 23°–27° C. Cultivation period is usually 20–28 hours.

The amidohydrolase contained in the cultured broth or its extract may be utilized in the present process without any further purification. The amidohydrolase enzyme may be precipitated with appropriate solvents, salted out or dialyzed or otherwise purified. It may be used free in solution or immobilized on an appropriate surface.

A method utilized in the present invention is that of utilizing the whole cell amidohydrolase preparation. By this method, after cultivation, the culture is centrifuged to obtain the whole cells for subsequent reaction.

The following are given for illustration purposes only and are not to be construed as limiting the scope of the present invention in any way.

EXAMPLE 1

Fifty ml. 2.5% yeast extract containing 0.08% neutralized (with NaOH) phenylacetic acid in a 250-ml. Erlenmeyer flask is inoculated with a tube of lyophilized culture of MB-2929 (*Escherichia coli* N.C.I.B. 8743). This flask is shaken at 25° C. at 240 rpm for 24 hours. A 35-ml. portion is centrifuged at 7500 rpm for 15 minutes. The supernatant is discarded and the pellet resuspended in 18 ml. distilled water. The solution is centrifuged at 7500 rpm for 15 minutes. The supernatant is discarded and the pellet taken up in 1 ml. of 0.05M potassium phosphate buffer, pH 7.4 to yield a whole cell amidohydrolase preparation which is then stored at 0° C.

The following reaction mixtures are incubated 18 hours at 23° C.

(1) A 10-μl. portion of whole cell amidohydrolase preparation plus 30 μl. of an approximately 1 mg./ml. solution of thienamycin plus 1 μl. neutralized 0.04M phenyl aceitc acid.

(2) A 10-μl. portion of whole cell amidohydrolase plus 30 μl. 50 mM potassium phosphate buffer, pH 7.4 plus 1 μl. neutralized 0.04M phenyl acetic acid.

(3) A 10-μl. portion of 0.05M potassium phosphate buffer, pH 7.4 plus 30 μl. of an approximately 1 mg./ml. solution of thienamycin.

After the 18 hours of incubation, 5-μl. aliquots of the reaction mixtures are applied to a cellulose-coated TLC plate, which is developed in EtOH:H$_2$O, 70:30. After air drying, the TLC plate is placed on a *Staphylococcus aureus* ATCC 6538P assay plate for 5 minutes.

The assay plates are prepared as follows: an overnight growth of the assay organism, *Staphylococcus aureus* ATCC 6538P, in nutrient broth plus 0.2% yeast extract is diluted with nutrient broth, plus 0.2% yeast extract to a suspension having 60% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Forty ml. of this suspension is poured into 22.5 cm. × 22.5 cm. petri plates, and these plates are chilled and held at 4° C. until used (5 day maximum).

The TLC plate is removed and the assay plate incubated overnight at 37° C.

The following bioactive spots are observed:
(1) $R_f$ 0.39–0.45 and 0.8;
(2) no bioactive spots;
(3) $R_f$ 0.39–0.45.

The bioactive spots at $R_f$ 0.39–0.45 are due to thienamycin. The bioactive spot at $R_f$ 0.8 is due to N-phenylacetyl thienamcyin.

What is claimed is:

1. A method for the preparation of N-acyl thienamycins having the following structure:

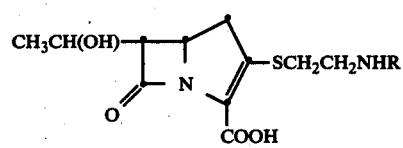

wherein R is an acyl radical produced by bringing the compound thienamycin having the following structure:

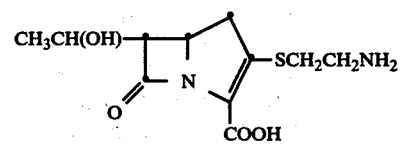

into contact with an acyl compound in an aqueous medium with a penicillin amidohydrolase which, when acting on the thienamycin substrate, produces the desired N-acylated thienamycin; wherein the acyl radical is represented by the formula:

wherein X is O or S and R' represents a straight or branched chain alkyl groups containing from 5-10 carbons, aryl, aryloxy groups containing 6-10 carbon atoms.

2. A process according to claim 1 wherein the penicillin amidohydrolase is designated E.C. 3.5.1.11 from *Escherichia coli*, N.C.I.B. 8743.

3. A process according to claim 1 wherein the acyl radical is represented by the formula:

wherein X is O or S and R' represents a straight or branched chain alkyl groups containing from 5-10 carbons, aryl, aryloxy groups containing 6-10 carbon atoms and wherein said groups are substituted with radicals selected from the group consisting of hydroxy, mercapto, alkyl, alkoxy, halo, amino, nitro and carboxy.

4. A process according to claim 1 wherein the acyl compound is selected from the group consisting of carboxylic acids, an amide thereof, a peptide thereof or a lower alkyl ester thereof.

5. A process according to claim 4 wherein the acyl compound is selected from the group consisting of phenyl acetic acid, p-hydroxyphenyl acetic acid, p-aminophenyl acetic acid, 3-hexenoic acid, methylphenyl acetate, methyl p-hydroxyphenyl acetate, methyl p-aminophenyl acetate, methyl 3-hexenoate, N-glycylphenyl acetate, n-glycyl p-hydroxyphenyl acetate, N-gylcyl p-aminophenyl acetate, N-glycyl 3-hexenoate, N-glycyl phenylglycinate and methyl phenylglycinate.

6. A process according to claim 5 wherein the acyl compound is selected from the group consisting of phenyl acetic acid, p-hydroxyphenyl acetic acid and p-aminophenyl acetic acid.

7. A process according to claim 5 wherein the acyl compound is phenyl acetic acid.

8. A process according to claim 1 wherein the acyl compound is selected from the group consisting of aryl carboxylic acids and lower alkyl esters thereof.

* * * * *